US00PP23219P2

(12) United States Plant Patent
Danziger

(10) Patent No.: US PP23,219 P2
(45) Date of Patent: Nov. 27, 2012

(54) ***VERBENA* PLANT NAMED 'DVER70'**

(50) Latin Name: *Verbena hybrida*
Varietal Denomination: DVER70

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/134,674

(22) Filed: Jun. 13, 2011

(51) Int. Cl.
*A01H 5/00* (2006.01)

(52) U.S. Cl. ..... Plt./308

(58) Field of Classification Search ..... Plt./308
See application file for complete search history.

*Primary Examiner* — Annette Para
(74) *Attorney, Agent, or Firm* — Cassandra Bright

(57) ABSTRACT

A new and distinct *Verbena* cultivar named 'DVER70' is disclosed, characterized by abundant, early flowering and a white flower color. Flowers on the new variety occur throughout the plant. The new variety is a *Verbena*, normally produced as an outdoor garden or container plant.

2 Drawing Sheets

Latin name of the genus and species: *Verbena hybrida*.
Variety denomination: 'DVER70'.

BACKGROUND OF THE INVENTION

The new *Verbena* cultivar is a product of a planned breeding program conducted by the inventor, Gavriel Danziger, in Moshav Mishmar Hashiva, Israel. The objective of the breeding program was to produce new *Verbena* varieties for ornamental commercial applications. The cross resulting in this new variety was made during July 2007.

The seed parent is the unpatented, proprietary seedling variety referred to as *Verbena hybrida* 'VE-7-1296' The pollen parent is unknown, as the crossing resulting in 'DVER70' was an open pollination, with unidentifiable pollen parents. The new variety was discovered in May 2008 by the inventor in a group of seedlings resulting from the 2007 crossing, in a research greenhouse in Moshav Mishmar Hashiva, Israel.

Asexual reproduction of the new cultivar 'DVER70' by vegetative cuttings was first performed at a research greenhouse in Moshav Mishmar Hashiva, Israel in May 2008 and has shown that the unique features of this cultivar are stable and reproduced true to type in successive generations.

SUMMARY OF THE INVENTION

The cultivar 'DVER70' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVER70' These characteristics in combination distinguish 'DVER70' as a new and distinct *Verbena* cultivar:

1. Highly floriferous
2. Early flowering
3. Flowers occurring throughout plant
4. Clear white flowers.

Plants of the new cultivar 'DVER70' are similar to plants of the seed parent, *Verbena hybrida* 'VE-7-1296' in most horticultural characteristics, however, plants of the new cultivar 'DVER70' have a more compact plant habit, and flowers more consistently. Additionally, the new cultivar has white flowers, whereas the seed parent has lavender flowers.

COMMERCIAL COMPARISON

Plants of the new cultivar 'DVER70' are comparable to the commercial variety *Verbena* 'BALAZPINK' U.S. Plant Pat. No. 14,529. The *Verbena* varieties are similar in most horticultural characteristics, however, plants of the new variety 'DVER70' differ in having a more vigorous growth habit, and different color flowers.

Plants of the new cultivar 'DVER70' can also be compared to the commercial variety *Verbena* 'USBENAL25' U.S. Plant Pat. No. 15,683. The *Verbena* varieties are similar in most horticultural characteristics, however, plants of the new variety 'DVER70' differ in having smaller foliage and different color flowers.

BRIEF DESCRIPTION OF THE PHOTOGRAPHS

Figure 1:
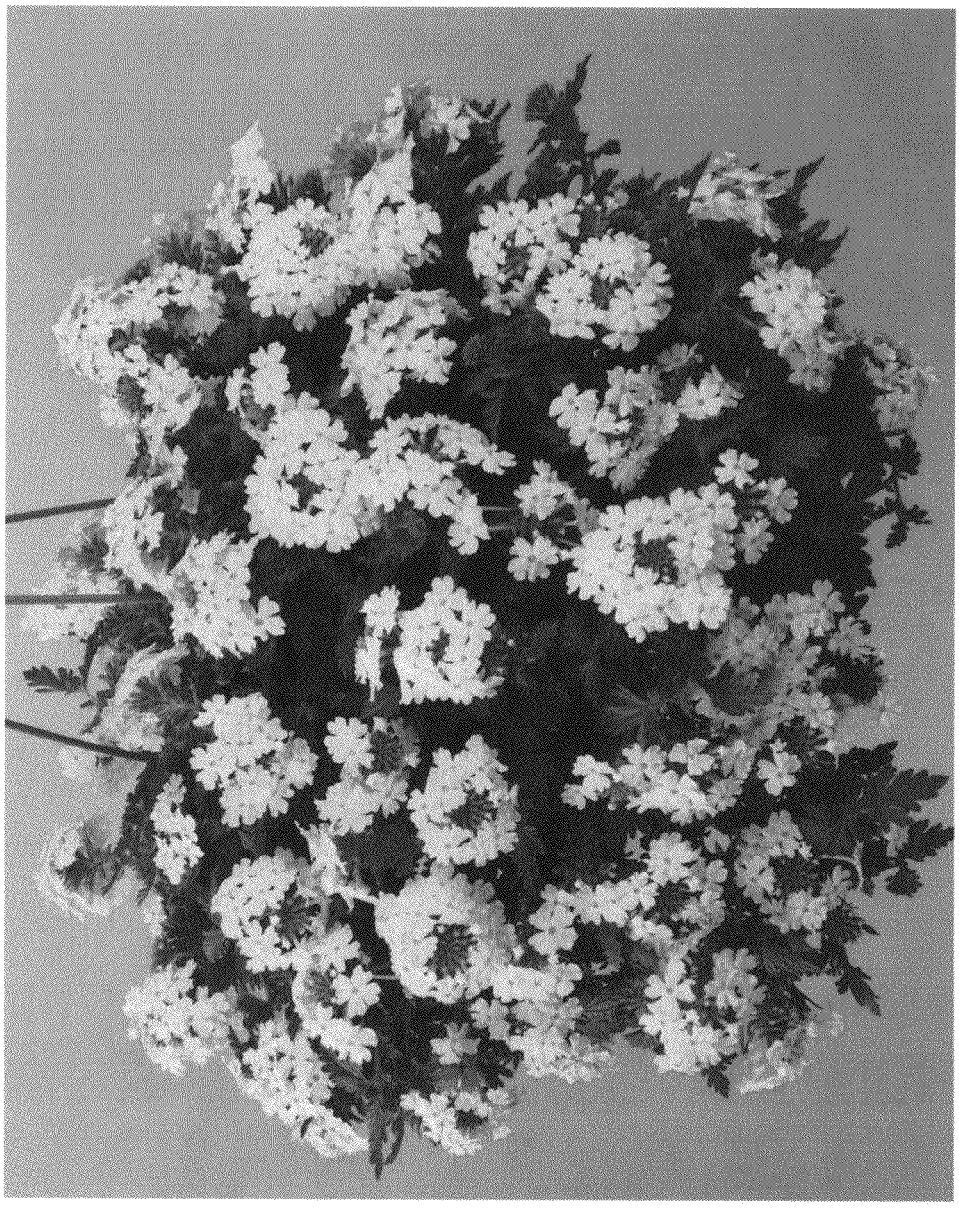

The accompanying photograph in FIG. 1 illustrates in full color a typical plant of 'DVER70' grown in a greenhouse, in a 13 cm basket. Age of the plant photographed is approximately 9 weeks from a rooted cutting.

Figure 2:
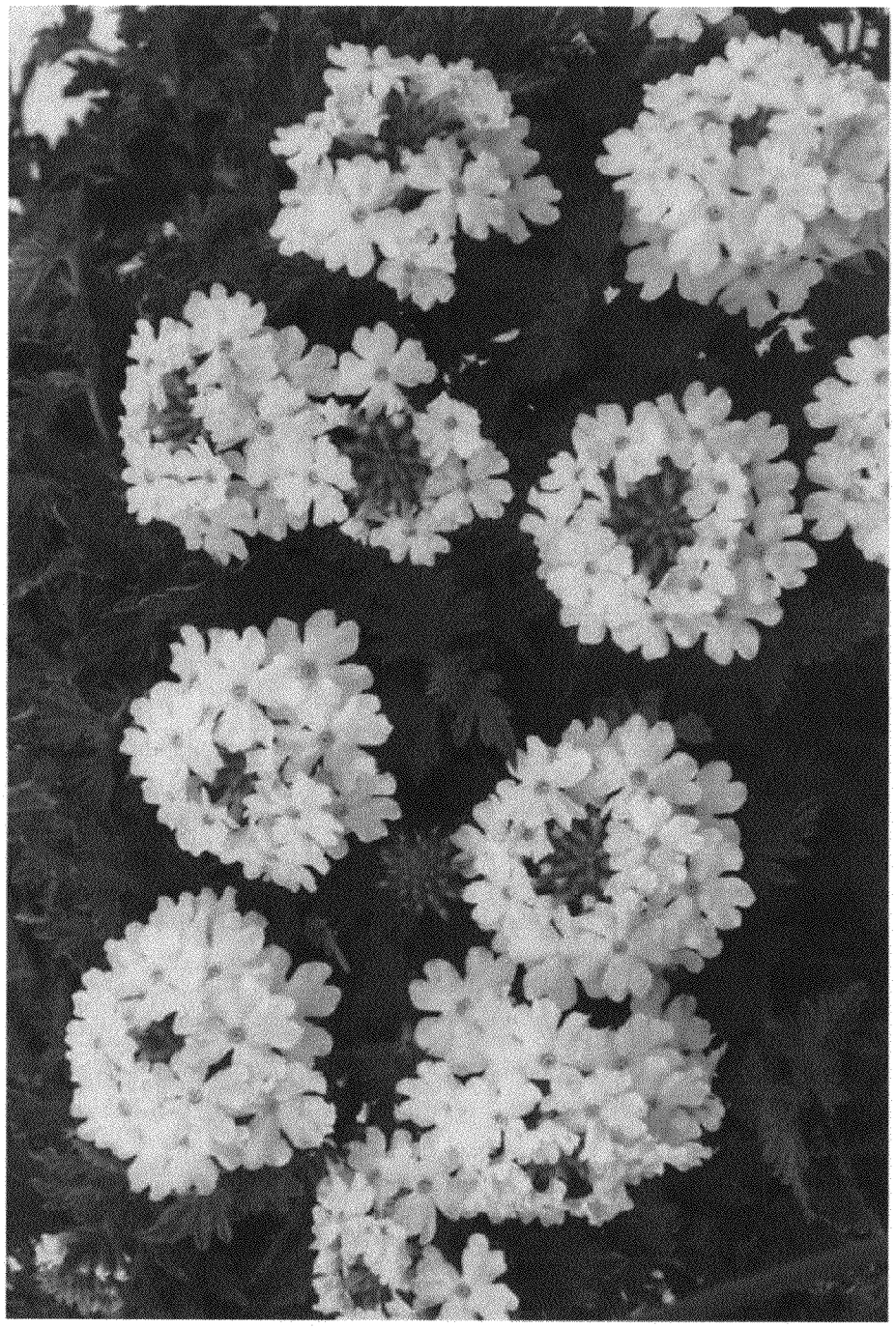

FIG. 2 illustrates in full color a close up of a typical bloom of 'DVER70'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DVER70' plants grown in a greenhouse during Spring and Summer in Mishmar Hashiva, Israel. The growing temperature ranged from 18° C. to 27° C. during the day and from 10° C. to 15° C. during the night. General light conditions are bright, normal sunlight. Measurements and numerical values represent averages of typical plant types. Botanical classification: *Verbena hybrida* 'DVER70'.

PROPAGATION

Time to initiate roots: 10 to 13 days at approximately 22° C.
Root description: Fibrous, spreading and dense.

PLANT

Pot size of plant described: 12 cm.
Age of plant described: Approximately 56 days.
Growth habit: Semi-upright.
Pot size of plant described: 12 cm.
Height: 12 cm.
Plant spread: 45 cm.
Growth rate: Fast.
Branching characteristics: Highly branched.
Length of primary lateral branches: 28 cm.
Diameter of lateral branches: 0.3 cm.
Quantity of primary lateral branches: 12.
Characteristics of primary lateral branches:
- *Form*.—Cylindrical.
- *Diameter*.—0.3 cm.
- *Color*.—Near RHS Green Group 137-B.
- *Texture*.—Pubescent.
- *Strength*.—Flexible.

Internode length: 2.3 cm.

FOLIAGE

- *Arrangement*.—Opposite.
- *Quantity*.—Approximately 14 per branch.
- *Average length*.—2.6 cm.
- *Average width*.—2.3 cm.
- *Shape of blade*.—Triangular.
- *Apex*.—Acute.
- *Base*.—Acuminate.
- *Margin*.—Incised.
- *Texture of top surface*.—Pubescent.
- *Pubescence*.—Strigose.
- *Aspect*.—90 degrees.
- *Color*.—Young foliage upper side: RHS Green group 143 C. Young foliage under side: RHS Yellow-Green group 147 C. Mature foliage upper side: RHS Yellow-Green group 147 A. Mature foliage under side: RHS Yellow-Green group 147 B.
- *Venation*.—Type: Venation color upper side: RHS Yellow-Green group 144 A. Venation color under side: RHS Yellow-Green group 145 C.
- *Petiole*.—Length: 0.5 cm. Diameter: 0.3 cm. Color: RHS Yellow-Green group 144 A. Texture: pubescent.

FLOWER

Natural flowering season: Spring/summer.
Days to flowering from rooted cutting: 23.
Inflorescence and flower type and habit: Simple corymb.
Rate of flower opening: 4 to 6 days from bud to fully opened flower.
Flower longevity on plant: 4 days.
Persistent or self-cleaning: Persistent.
Bud:
- *Shape*.—Quinquangular.
- *Length*.—1.2 cm.
- *Diameter*.—1 cm.
- *Color*.—Near RHS Yellow-Green 145A.

Corolla:
- *Petals/lobes*.—Number: 5. Length: 0.6 cm. Width: 0.5 cm. Shape: similar to obcordate. Aspect: upright. Margin: entire. Texture: smooth. Color: When opening: Upper surface: RHS White N999D. Lower surface: RHS White N999D. Fully opened: Upper surface: RHS White N999D. Lower surface: RHS White N999D.
- *Throat*.—Color: Near RHS White 155A. Texture: smooth.
- *Tube color*.—Near RHS Green-White 157A.

Calyx:
- *Form*.—Fused.
- *Length*.—1 cm.
- *Diameter*.—2 cm.
- *Sepal shape*.—Quinquangular.
- *Sepal margin*.—Entire.
- *Sepal texture*.—Strigose.
- *Sepal color*.—Upper surface: Near RHS Yellow-Green 144A. Lower surface: Near RHS Yellow-Green 144D.

Fragrance: None.

REPRODUCTIVE ORGANS

Stamens:
- *Number (per flower)*.—4.
- *Filament length*.—0.2 cm.
- *Anthers*.—Shape: oval. Length: 0.1 cm. Color: RHS Yellow-Green N144A.

Pollen: Color: RHS Yellow-Green N144B. Amount: abundant.
Pistils:
- *Quantity per flower*.—1.
- *Length*.—1.6 cm.
- *Styles*.—Length: 1.3. Color: RHS Yellow-Green 149-D.
- *Stigma*.—Shape: ovoid. Color: RHS Yellow-Green N144C.

OTHER CHARACTERISTICS

Seeds and fruits: Not observed to date.
Disease/pest resistance: Tolerant of Powdery Mildew.
Temperature tolerance: High temperature tolerance to at least 30° C.

What is claimed is:

1. A new and distinct cultivar of *Verbena* plant named 'DVER70' as herein illustrated and described.

* * * * *